US010695205B2

(12) United States Patent
Vad

(10) Patent No.: US 10,695,205 B2
(45) Date of Patent: Jun. 30, 2020

(54) SYSTEMS AND METHODS FOR SECURING AND RELEASING A PORTION OF A STENT

(71) Applicant: COOK MEDICAL TECHNOLOGIES LLC, Bloomington, IN (US)

(72) Inventor: Siddharth Vad, Irvine, CA (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 461 days.

(21) Appl. No.: 15/601,470

(22) Filed: May 22, 2017

(65) Prior Publication Data

US 2017/0252193 A1 Sep. 7, 2017

Related U.S. Application Data

(62) Division of application No. 14/105,883, filed on Dec. 13, 2013, now Pat. No. 9,687,373.

(60) Provisional application No. 61/745,200, filed on Dec. 21, 2012.

(51) Int. Cl.
*A61F 2/966* (2013.01)
*A61F 2/95* (2013.01)
*A61F 2/07* (2013.01)

(52) U.S. Cl.
CPC ........ *A61F 2/966* (2013.01); *A61F 2002/075* (2013.01); *A61F 2002/9505* (2013.01); *A61F 2220/0033* (2013.01); *A61F 2230/0013* (2013.01); *A61F 2230/0052* (2013.01); *A61F 2230/0058* (2013.01)

(58) Field of Classification Search
CPC ........ A61F 2002/075; A61F 2002/9505; A61F 2/966; A61F 2220/0033; A61F 2230/0013; A61F 2230/0052; A61F 2230/0058
See application file for complete search history.

(56) References Cited

U.S. PATENT DOCUMENTS 4,471,777 A * 9/1984 McCorkle, Jr. ...... A61B 17/221
                                                    294/100
5,201,757 A    4/1993 Heyn et al.
5,480,423 A    1/1996 Ravenscroft et al.
(Continued)

FOREIGN PATENT DOCUMENTS

DE  102006053748   4/2008
EP      1440673    7/2004
(Continued)

OTHER PUBLICATIONS

European Search Report for Application No. 13171753 dated Oct. 21, 2013, 7 pgs.
(Continued)

*Primary Examiner* — Julie A Szpira
(74) *Attorney, Agent, or Firm* — Brinks Gilson & Lione

(57) ABSTRACT

The present embodiments provide systems and methods for deploying at least a portion of a stent, comprising a retaining member having a main body. At least one slot is formed into the main body. The at least one slot comprises a circumferentially enclosed segment and an axial opening. A portion of a stent is restrained from moving radially outward when disposed within the circumferentially enclosed segment, and the portion of the stent is self-expandable radially outward when aligned with the axial opening.

20 Claims, 6 Drawing Sheets

(56) References Cited

U.S. PATENT DOCUMENTS

| | | | |
|---|---|---|---|
| 5,824,041 A | 10/1998 | Lenker et al. | |
| 5,824,058 A | 10/1998 | Ravenscroft | |
| 5,868,706 A * | 2/1999 | Cox | A61M 25/09033 604/524 |
| 6,077,296 A | 6/2000 | Shokoohi et al. | |
| 6,623,518 B2 * | 9/2003 | Thompson | A61F 2/91 606/108 |
| 6,872,224 B1 | 3/2005 | Telxelra Moretra et al. | |
| 7,101,390 B2 | 9/2006 | Nelson | |
| 7,147,657 B2 | 12/2006 | Chiang | |
| 7,264,632 B2 | 9/2007 | Wright | |
| 7,297,156 B2 | 11/2007 | Nelson | |
| 7,335,224 B2 | 2/2008 | Ohlenschlaeger | |
| 7,611,528 B2 | 11/2009 | Goodson, IV | |
| 7,632,298 B2 | 12/2009 | Hijlkema et al. | |
| 7,815,671 B2 | 10/2010 | Wright et al. | |
| 7,909,863 B2 | 3/2011 | Hartley et al. | |
| 7,942,924 B1 * | 5/2011 | Perez | A61F 2/966 623/1.23 |
| 7,959,661 B2 | 6/2011 | Hijlkema et al. | |
| 8,043,354 B2 | 10/2011 | Greenberg et al. | |
| 8,062,345 B2 | 11/2011 | Ouellette et al. | |
| 8,109,986 B2 | 2/2012 | Styrc | |
| 9,119,717 B2 * | 9/2015 | Wang | A61F 2/2436 |
| 9,439,795 B2 * | 9/2016 | Wang | A61F 2/2436 |
| 9,918,837 B2 * | 3/2018 | Glazier | A61F 2/2418 |
| 2004/0267348 A1 * | 12/2004 | Gunderson | A61F 2/91 623/1.12 |
| 2005/0049674 A1 | 3/2005 | Berra et al. | |
| 2006/0100688 A1 * | 5/2006 | Jordan | A61F 2/95 623/1.12 |
| 2006/0111771 A1 * | 5/2006 | Ton | A61F 2/88 623/1.15 |
| 2006/0259120 A1 * | 11/2006 | Vongphakdy | A61F 2/95 623/1.11 |
| 2007/0293930 A1 * | 12/2007 | Wang | A61F 2/91 623/1.11 |
| 2008/0264102 A1 | 10/2008 | Berra | |
| 2009/0030497 A1 | 1/2009 | Metcalf et al. | |
| 2009/0099637 A1 | 4/2009 | Barthold et al. | |
| 2009/0099640 A1 | 4/2009 | Weng | |
| 2009/0192585 A1 | 6/2009 | Bloom et al. | |
| 2009/0287290 A1 * | 11/2009 | Macaulay | A61F 2/2412 623/1.11 |
| 2009/0287299 A1 | 11/2009 | Tabor et al. | |
| 2009/0306761 A1 * | 12/2009 | Hebert | A61F 2/91 623/1.12 |
| 2010/0010617 A1 | 1/2010 | Goodson, IV et al. | |
| 2010/0249896 A1 | 9/2010 | Sugimoto et al. | |
| 2010/0324647 A1 | 12/2010 | Rincon | |
| 2011/0251664 A1 | 10/2011 | Acevedo | |
| 2011/0257720 A1 * | 10/2011 | Peterson | A61F 2/95 623/1.11 |
| 2011/0264202 A1 * | 10/2011 | Murray, III | A61F 2/2418 623/2.11 |
| 2012/0010696 A1 | 1/2012 | Greenberg et al. | |

FOREIGN PATENT DOCUMENTS

| | | |
|---|---|---|
| EP | 2266509 | 8/2013 |
| WO | WO 2000/065270 A1 | 11/2000 |
| WO | WO 2007/092276 A1 | 8/2007 |
| WO | WO 2008/098255 A1 | 8/2008 |
| WO | WO 2009/042789 A1 | 4/2009 |
| WO | WO 2009/098255 A1 | 8/2009 |
| WO | WO 2009/134801 A1 | 11/2009 |
| WO | WO 2012/068175 A1 | 5/2012 |

OTHER PUBLICATIONS

European Search Report for Application No. 10166254 dated Oct. 31, 2010, 2 pgs.

Extended European Search Report for Application No. 13275315.3 dated Apr. 4, 2014, 7 pgs.

Response to Extended European Search Report for Application No. 13275315.3 filed Dec. 12, 2014, 11 pgs.

* cited by examiner

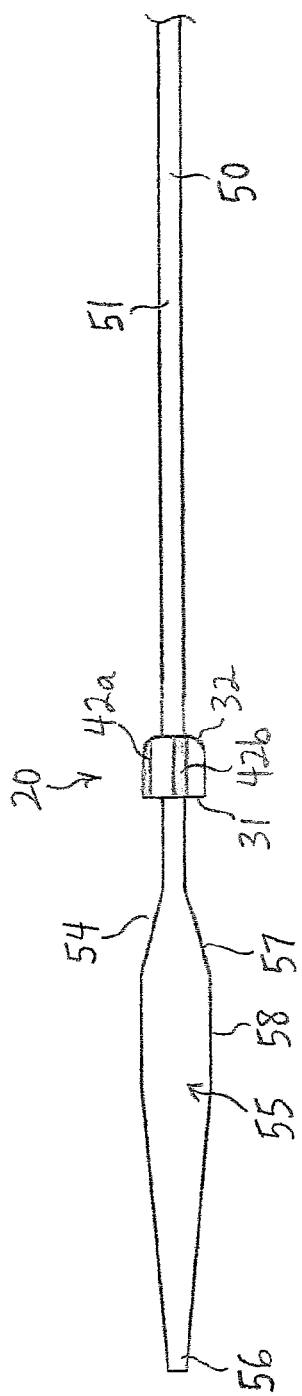
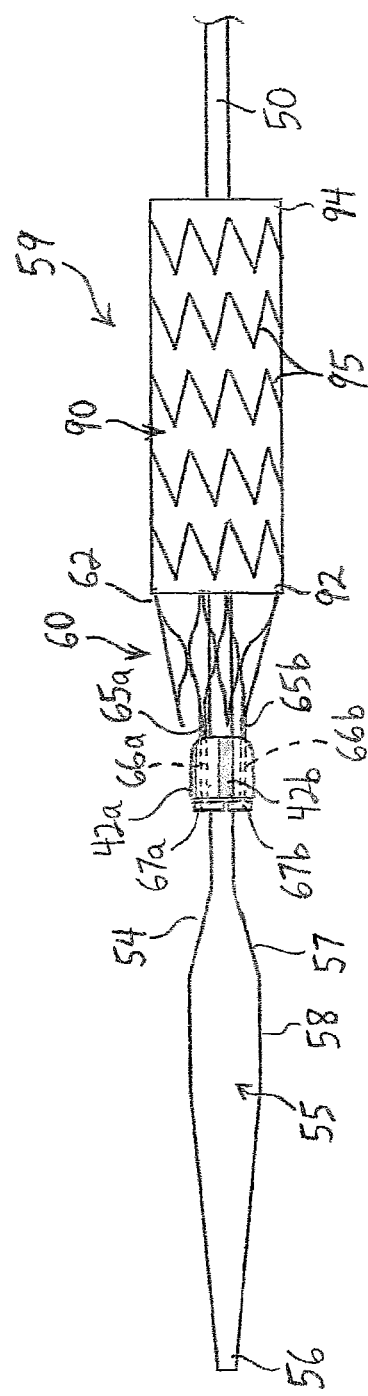

SYSTEMS AND METHODS FOR SECURING AND RELEASING A PORTION OF A STENT

PRIORITY CLAIM

The present patent document is a divisional application that claims the benefit of priority under 35 U.S.C. § 121 of U.S. patent application Ser. No. 14/105,883, filed Dec. 13, 2013, which claims priority under 35 U.S.C. § 119 to U.S. Provisional Patent Application Ser. No. 61/745,200, filed Dec. 21, 2012, each of which is hereby incorporated by reference in its entirety.

BACKGROUND

The present embodiments relate generally to apparatus and methods for treating medical conditions, and more specifically, to systems and methods for securing and releasing a portion of a stent.

Stents may be inserted into an anatomical vessel or duct for various purposes. Stents may maintain or restore patency in a formerly blocked or constricted passageway, for example, following a balloon angioplasty procedure. Other stents may be used for different procedures, for example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they can have characteristics of both types of stents. Self-expanding stents may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as nitinol, the shape-memory alloy may be employed to cause the stent to return to a predetermined configuration upon removal of the sheath or other device maintaining the stent in its predeployment configuration.

When trigger wires are used as a deployment control mechanism, the trigger wires may releasably couple the proximal and/or distal ends of a stent or stent-graft to a delivery catheter. Typically, one or more trigger wires are looped through a portion of the stent near a vertex of the stent. For example, trigger wires may be used to restrain a "Z-stent" or Gianturco stent comprising a series of substantially straight segments interconnected by a series of bent segments. The trigger wires may be disposed through, and pull upon, the bent segments to pull the stent closely against the delivery catheter.

Trigger wires also may be used in conjunction with different stent designs, such as cannula-cut stents having relatively acute or pointed bends. The designs of cannula-cut stents may facilitate compression of the stent to a relatively small delivery profile due to the tight bends of the apices. With such stents, the trigger wires may be looped around one or more vertices formed beneath the proximal and/or distal apices, e.g., a location where an individual apex splits into two separate strut segments.

If trigger wires are threaded through the vertices of such cannula-cut stents, the trigger wires may become crimped at the vertices during compression of the stent to a reduced diameter delivery profile. If the trigger wires are crimped between the strut segments, the trigger wires and/or stent segments may become damaged during delivery, particularly for nickel-titanium stents that may be sensitive to surface imperfections. Furthermore, when compressing a cannula-cut stent having relatively acute bends to a significantly reduced radial profile, barbs disposed near the apices of the stent may become entangled with the stent struts and/or the trigger wires. Still further, in some instance, trigger wires may require a relatively high deployment force when being retracted, and the provision of multiple trigger wires may add to the profile of the delivery system.

SUMMARY

The present embodiments provide systems and methods for deploying at least a portion of a stent, comprising a retaining member having a main body. At least one slot is formed into the main body. The at least one slot comprises a circumferentially enclosed segment and an axial opening. A portion of a stent is restrained from moving radially outward when disposed within the circumferentially enclosed segment, and the portion of the stent is self-expandable radially outward when aligned with the axial opening.

The portion of the stent may comprise a first width that is less than a second width of the axial opening of the retaining member. The axial opening may extend longitudinally between first and second ends of the main body of the retaining member.

At least a portion of the retaining member may be secured to an outer surface of a cannula. Circumferential rotation of the cannula relative to the stent may cause corresponding rotation of the retaining member relative to the stent, thereby rotating the portion of the stent within the circumferentially enclosed segment of the slot.

The main body of the retaining member may comprise a lumen extending between the first and second ends, where the cannula extends through the lumen of the retaining member. The second end of the main body may be tapered radially inward towards the cannula.

In one embodiment, the stent may comprise at least one coupling portion comprising a longitudinal strut portion having the first width that is less than the second width of the axial opening of the retaining member. The coupling portion may extend proximally from a proximal apex of the stent. The coupling portion may comprise a projection. In one example, the longitudinal strut portion and the projection of the coupling portion collectively may form a "t" shape. The lateral projection may be disposed proximal to the first end of the main body of the retaining member when the stent is restrained.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 3 is a side view depicting the retaining member of FIGS. 1-2 being coupled to a cannula.

FIG. 4 is a side view depicting a portion of a stent being secured to the retaining member when it is coupled to the cannula of FIG. 3.

DETAILED DESCRIPTION OF THE PREFERRED EMBODIMENTS

Figure 2:
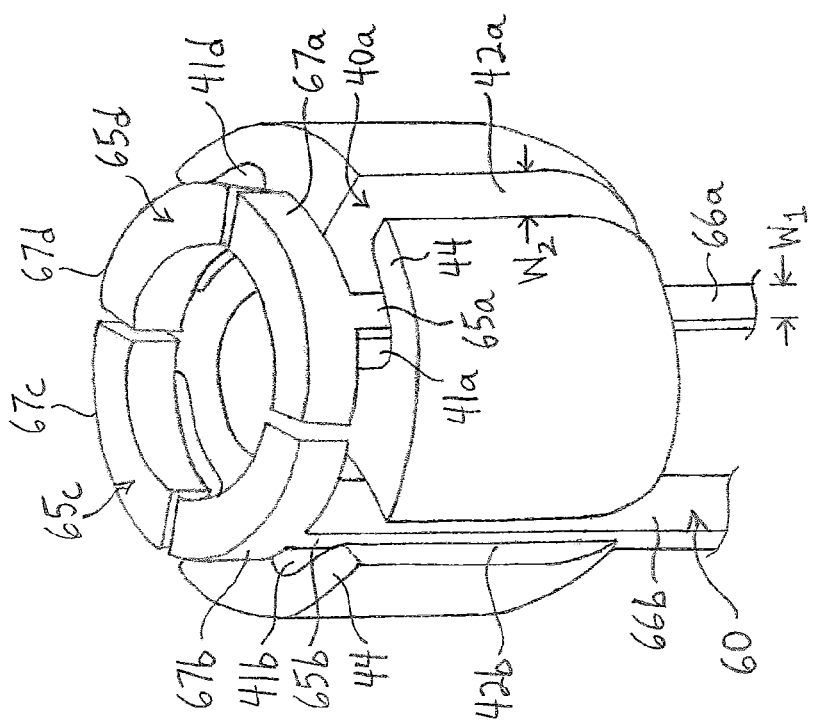
FIG. 2 is an elevated perspective view depicting a portion of a stent being secured to the retaining member of FIG. 1.

In the present application, the term "proximal" refers to a direction that is generally closest to the heart during a medical procedure, while the term "distal" refers to a direction that is furthest from the heart during a medical procedure.

Referring to FIGS. 1-4, a first embodiment of a retaining member 20 is shown for deploying a portion of a stent. The retaining member 20 generally comprises a main body 30 having a first end 31 and a second end 32. In the present embodiments, the first end 31 is generally depicted as being the proximal end when positioned inside of a body, and the second end 32 is depicted as being the distal end, however the relative axial positions of the first and second ends 31 and 32 may be switched in alternative embodiments. Further, while the main body 30 of the retaining member 20 is depicted as having a generally cylindrical shape in the present embodiments, it is contemplated that shapes other than cylindrical may be used.

Figure 1:
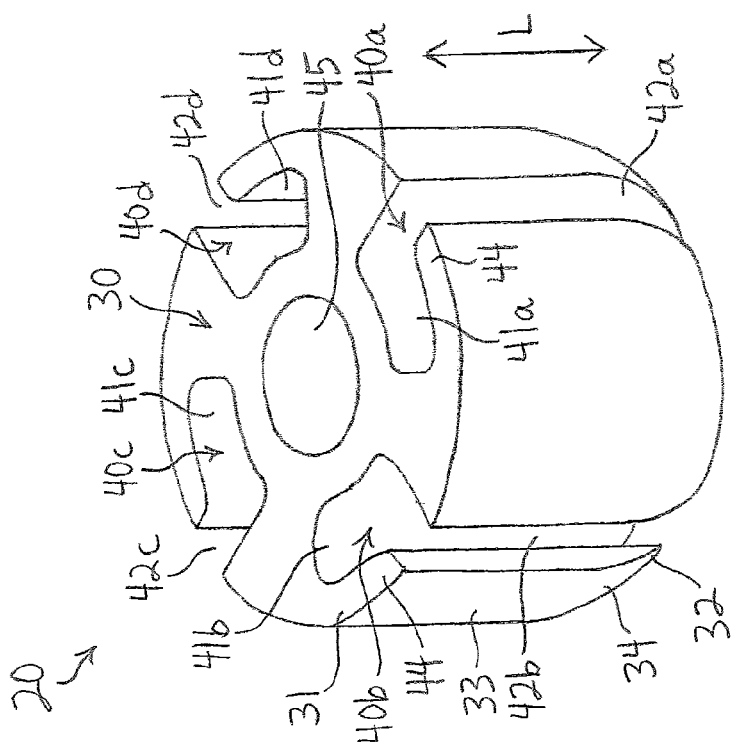
FIG. 1 is an elevated perspective view of a retaining member of the present embodiments.

The main body 30 has a longitudinal segment 33 disposed between the first and second ends 31 and 32, which is generally parallel to a longitudinal axis L of the retaining member 20, as depicted in FIG. 1. Further, the main body 30 optionally comprises a tapered segment 34, which reduces the diameter of the main body 30 in a radially inward direction from the longitudinal segment 33 towards the second end 32, as shown in FIG. 1. The tapered segment 34 may provide a contoured segment that facilitates removal of the retaining member 20 after deployment of a stent, as described below.

The retaining member 20 further comprises a plurality of slots 40. In the non-limiting example of FIGS. 1-4, the retaining member 20 comprises four slot 40a-40d, although greater or fewer slots may be employed.

Each of the slots 40a-40d comprises a circumferentially enclosed segment 41a-41d, and further comprises an axial opening 42a-42d. A portion of each circumferentially enclosed segment 41a-41d is enclosed by an outer wall portion 44. The axial openings 42a-42d are at one end of each circumferentially enclosed segment 41a-41d, respectively, and are not enclosed by an outer wall portion 44, as best seen in FIG. 1.

In an embodiment having four slots 40a-40d, each of the circumferentially enclosed segments 41a-41d may span between about 10 and 85 degrees around a circumference of the main body 30. Further, each of the slots 40a-40d may be spaced apart at equal distances from one another, and generally symmetrical to one another, as depicted in FIG. 1. The slots 40a-40d may be formed in the main body 30 by any suitable technique, including but not limited to later cutting, extrusion, and the like.

The retaining member 20 further comprises a lumen 45, which extends longitudinally between the first and second ends 31 and 32 of the main body 30. The lumen 45 may be centrally disposed within the main body 30, and comprises an inner diameter that is slightly larger than an outer diameter of a cannula 50, as shown in FIGS. 3-4. The retaining member 20 is dimensioned to be secured to an outer surface 51 of the cannula 50, e.g., by welding, soldering, a frictional fit, or other suitable technique.

The cannula 50 of FIGS. 3-4 may be incorporated as part of a broader stent or stent-graft delivery system, and may span a longitudinal length in which a distal segment extends outside of a patient's body, and a proximal segment 54, including the retaining member 20, is delivered towards a target site inside of a patient's body. In the embodiment of FIGS. 3-4, one or more outer cannulas or sheaths may be disposed coaxially over the cannula 50 during delivery. For example, an exemplary stent-graft 59 may be disposed over an exterior surface of the cannula 50 and within one or more outer cannulas or sheaths, thereby encompassing the stent-graft during a delivery stage.

The cannula 50 may comprise a tubular member having a lumen sized to allow the cannula 50 to be advanced over a wire guide during delivery. A proximal region of the cannula 50 may be integrally formed with, or externally coupled to, an atraumatic tip 55. The atraumatic tip 55 may comprise proximal and distal regions 56 and 57, respectively, and a central region 58 disposed therebetween. The proximal and distal regions 56 and 57 comprise a smaller outer diameter relative to the central region 58, with a first taper allowing for a smooth transition between the proximal region 56 and the central region 58, and a second taper allowing for a smooth transition between the distal region 57 and the central region 58.

Figure 7:
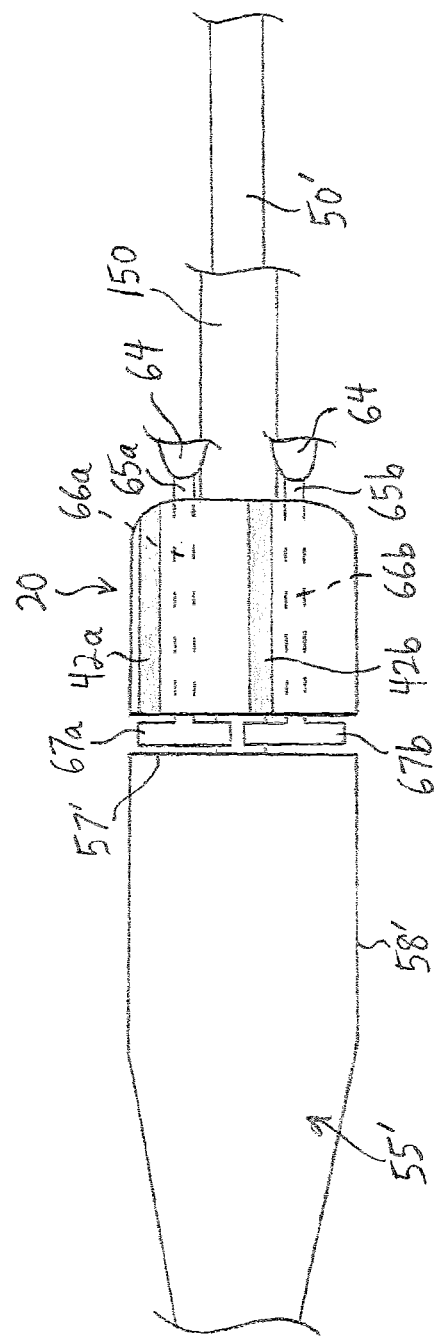
FIGS. 7-8 are, respectively, side views depicting first and second states of an alternative embodiment in which the retaining member of FIG. 1 is used in a system with inner and outer cannulas.

In one example, the retaining member 20 may be spaced distally away from the atraumatic tip 55, as depicted in FIGS. 3-4. In alternative embodiments, however, the retaining member 20 may be positioned in close proximity to the atraumatic tip, for example, as depicted in FIG. 7 below. Further, an outer diameter of the main body 30 of the retaining member 20 preferably is less than or equal to an outer diameter at the central region 58 of the atraumatic tip 55, and therefore the provision of the retaining member 20 does not increase the overall profile of the delivery system.

Figure 5:
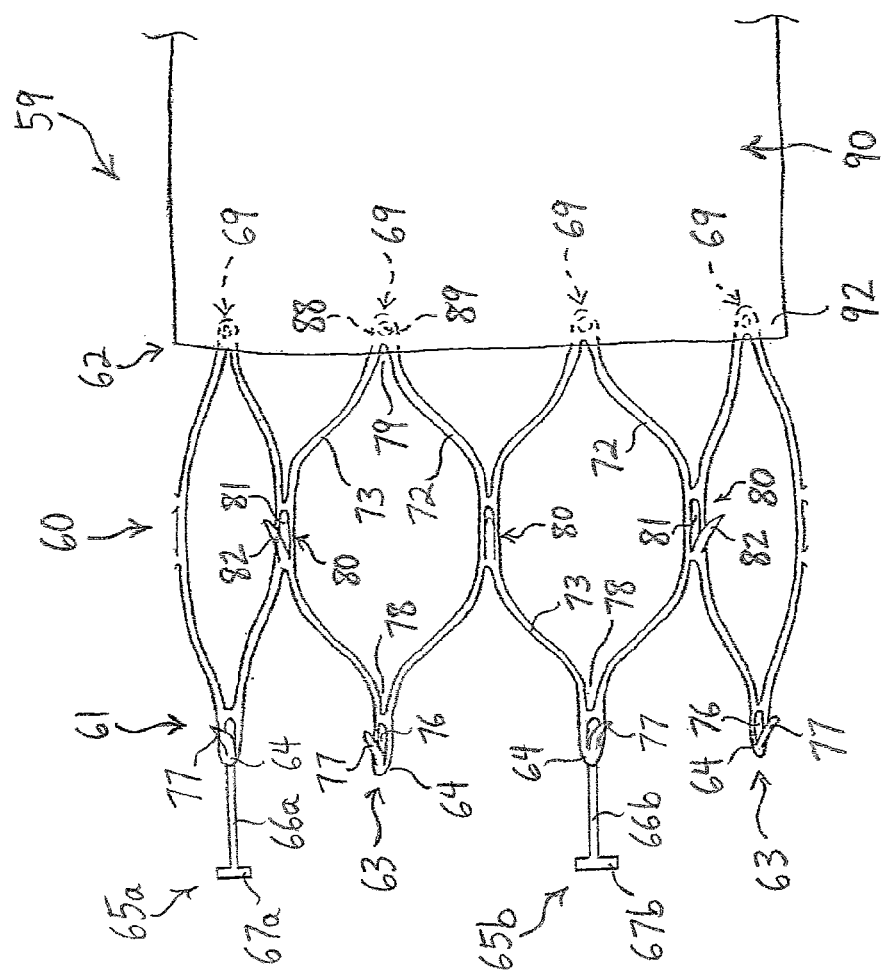
FIG. 5 depicts an exemplary stent-graft having a portion that may be deployed using the retaining member of FIGS. 1-4.

Referring to FIGS. 2, 4 and 5, an exemplary stent-graft 59, having a proximally-located stent 60 coupled to a graft material 90, may be deployed in a controlled manner using the retaining member 20. In this non-limiting embodiment, the stent 60 may be manufactured from a continuous cylinder into which a pattern may be cut by a laser or by chemical etching to produce slits in the wall of the cylinder. The resulting structure may then be heat set to give it a desired final configuration. As shown in FIG. 5, the final configuration may include a shape having a series of proximal apices and a series of distal apices. A proximal end 61 of the stent 60 may comprise multiple adjacent proximal apices 63, while a distal end 62 of the stent 60 may comprise multiple adjacent distal apices 69, as best seen in FIG. 5.

One or more of the proximal apices 63 may comprise an end region 64 having an integral barb 77 formed therein. The barb 77 may be formed by laser cutting a desired barb shape into the end regions 64. A slit 76 therefore is formed into each end region 64 after the desired barb shape is formed, as shown in FIG. 5. Once the desired barb shape is cut, a main body of the barb 77 may be bent in a radially outward direction with respect to the end region 64. The angle may comprise any acute angle, or alternatively may be substantially orthogonal or obtuse. If desired, the barb 77 may be sharpened, for example, by grinding the tip of the barb, to facilitate engagement at a target tissue site. While each of the proximal apices 63 are depicted as having barbs in FIG. 5, in alternative embodiments fewer than all of the proximal apices may comprise barbs.

At least one of the proximal apices 61 of the stent 60 further comprises a coupling portion 65, which extends proximally away from its respective end region 64. In the example shown, every other proximal apex 63 comprises a coupling portion 65. Therefore, in the non-limiting, illustrative example in which the stent 60 comprises eight proximal apices 61 formed into a cylindrical shape, there will be four coupling portions 65a-65d disposed in a generally cylindrical manner, as best seen in FIG. 2. It will be appreciated that greater or fewer than four coupling portions may be provided in the example where the stent has eight proximal apices. In one alternative, each of the proximal apices may comprise a coupling portion.

Each of the coupling portions 65a-65d may comprise a longitudinal strut portion 66 and a projection 67, which in certain examples may be a lateral projection. The longitudinal strut portions 66 have distal segments that extend from the end region 64, and have proximal segments that transition into the projection 67. In the non-limiting examples depicted herein, the coupling portions 65 generally comprise a "t-shape" formed collectively by the longitudinal strut portions 66 and the projections 67. The provision of projections 67a-67d may reduce inadvertent premature deployment of the coupling portions 65a-65d from their respective slots 40a-40d, as described further below. In particular, the stent 60 may be inclined to move in a distal direction prior to deployment. However, the projections 67a-67d, which at least partially circumferentially and/or radially overlap with solid regions of the main body 30, are precluded from moving distally beyond the first end 31 of the retaining member 20 in the delivery state.

Each of the longitudinal strut portions 66 comprises a width $w_1$, which is less than a width $w_2$ of a respective axial opening 42a-42d of the retaining member 20, as depicted in FIG. 2. Accordingly, the longitudinal strut portions 66a-66d are releasable from the respective slots 40a-40d of the retaining member 20, as described in further detail below.

Referring still to FIG. 5, the stent 60 may comprise multiple angled strut segments disposed between each of the proximal apices 63 and each of the distal apices 69. By way of example, a first proximal apex 63 extends distally and splits into first and second angled strut segments 72 and 73, respectively, thereby forming a proximal vertex 78, as shown in FIG. 5. In a compressed state, the first and second angled strut segments 72 and 73 may be compressed such that they are substantially parallel to one another. Similarly, each distal apex 69 may extend in a proximal direction and split into the first and second angled strut segments 72 and 73, respectively, thereby forming a distal vertex 79. A first angled strut segments 72 may meet with an adjacent second angled strut segment 73, thereby forming a transition region 80. In this manner, the stent 60 may be formed into a continuous, generally cylindrical shape, as shown in FIG. 5.

Expansion of the stent 60 is at least partly provided by the angled strut segments 72 and 73, which may be substantially parallel to one another in a compressed state, but may tend to bow outward away from one another in the expanded state shown in FIG. 5. The stent 60 may be formed from any suitable material, such as a laser-cut nitinol cannula. If manufactured from nitinol, the stent 60 may be inclined to assume the expanded state shown in FIG. 5 upon removal of a constraining external forces.

Each transition region 80 may comprise a larger surface area relative to the angled segments, since the transition regions are composed substantially of multiple different angled segments 72 and 73. The stent 60 may comprise at least one barb 82 disposed in at least one of the transition regions 80. The barb 82 may be formed integrally, as part of the strut, or may comprise an external barb that is adhered to a surface of the transition regions 80. As shown in FIG. 5, multiple integral barbs 82 are provided. Like the barbs 77 noted above, the barbs 82 may be formed by laser cutting a desired barb shape into the transition regions 80. A slit 81 therefore is formed into the transition region 80 after the desired barb shape is formed, as shown in FIG. 5. Since the transition regions 80 may comprise an increased surface area relative to other regions of the stent 60, it may be easier to perforate portions of the transition regions 80 without adversely affecting the structural integrity of the stent. Once the desired barb shape is cut, a main body of the barb 82 may be bent in an outward direction at any angle with respect to the transition region 80 and optionally may be sharpened to facilitate engagement at a target tissue site.

Each of the distal apices 69 may comprise an end region 88 having a bore 89 formed therein, as shown in FIG. 5. The distal end 62 of the stent 60 may be coupled to a proximal end 92 of the graft material 90. The distal apices 69 may be coupled to the graft material, for example, using one or more sutures that are looped through the graft material and the bores 89 of the stent 60. In this manner, the stent 60 may be used as an attachment stent for endovascular graft fixation. For example, the graft material 90 may overlap with an aneurysm to seal off fluid flow into the aneurysm, while the proximal end 61 of the stent 60 may extend in a proximal direction away from the graft material, e.g., to engage a healthy portion of a vessel wall away from a diseased portion of the aneurysm. As will be apparent, one or more additional stents may be coupled to an inner or outer surface of the graft material 90, i.e., at a location distal to the stent 60, to help maintain patency throughout the graft material. While multiple exemplary zig-zag stents 95 are shown coupled to the graft material 90 between the proximal and distal ends 92 and 94 of the graft material 90 in FIG. 4, it will be apparent than any shape of stent may be used, and such stents may be coupled to either the inner or outer surfaces of the graft material 90.

The stent 60 has a reduced diameter delivery state so that it may be advanced to a target location within a vessel or duct. The stent 60 also has an expanded deployed state to apply a radially outward force upon at least a portion of a vessel or duct, e.g., to maintain patency within a passageway, or to hold open the lumen of a graft. In the expanded state, fluid flow is allowed through a central lumen of the stent 60. Further, the struts of the stent 60 may comprise a substantially flat wire profile or may comprise a rounded profile. As best seen in FIG. 2, the struts of the stent 60 generally comprise a flat wire profile.

The stent 60 may be manufactured from a super-elastic material. Solely by way of example, the super-elastic material may comprise a shape-memory alloy, such as a nickel titanium alloy (nitinol). If the stent 60 comprises a self-expanding material such as nitinol, the stent may be heat-set into the desired expanded state, whereby the stent 60 can assume a relaxed configuration in which it assumes the preconfigured first expanded inner diameter upon application of a certain cold or hot medium. Alternatively, the stent 60 may be made from other metals and alloys that allow the stent 60 to return to its original, expanded configuration upon deployment, without inducing a permanent strain on the material due to compression. Solely by way of example, the stent 60 may comprise other materials such as stainless steel, cobalt-chrome alloys, amorphous metals, tantalum, platinum, gold and titanium. The stent 60 also may be made from non-metallic materials, such as thermoplastics and other polymers.

While one exemplary stent 60 is shown in FIGS. 2, 4 and 5, various alternative stent configurations may be used in conjunction with the retaining member 20 of FIGS. 1-4. Moreover, the stent may be deployed alone, or as part of a stent-graft system, as depicted herein.

Referring to FIGS. 2 and 4, an exemplary coupling of a portion of the stent-graft 59 and associated stent 60 to the deployment apparatus of FIG. 3 is shown and described. The stent-graft 59 has an uncoupled state in which the stent-graft 59 is positioned coaxially over the cannula 50 with the each of the coupling portions 65a-65d being aligned with a respective slot 40a-40d of the retaining member 20. In particular, the longitudinal strut portion 66a of the coupling portion 65a is compressed in a radially inward direction within the axial opening 42a of the retaining member 20. Similar, the other longitudinal strut portions 66b-66d are compressed into their respective axial openings 42b-42d of the retaining member 20.

A secure engagement between the stent 60 and the retaining member 20 is achieved by rotating the cannula 50, and therefore the retaining member 20, in a counterclockwise direction until the longitudinal strut portions 66a-66d are aligned within their respective circumferentially enclosed segments 41a-41d of the retaining member 20, as depicted in FIG. 2. At this time, the longitudinal strut portions 66a-66d are precluded from radially outward deployment due to overlap with the outer wall portions 44, and in other words, by misalignment from the axial openings 42a-42d. At this time, each of the projections 67a-67d may be disposed proximal to the first end 61 of the retaining member 20, as depicted in FIGS. 2 and 4.

The coupling shown in FIG. 2 and FIG. 4 secures the stent 60 to the cannula 50 via the retaining member 20 in a manner that may subsequently facilitate insertion of the subassembly comprising the cannula 50 and the stent-graft 59 into an outer sheath. As will be apparent, the outer sheath is configured to radially restrain other regions of the stent-graft 59 for delivery to a target site within a patient's anatomy.

In this embodiment, the coupling portions 65a-65d are coupled to every other proximal apex 63 to restrain the stent 60 during delivery. By restraining the alternating proximal apices 63 that comprise coupling portions 65, the adjacent proximal apices without coupling portions also may be indirectly pulled in a radially inward direction during delivery. The configuration of the stent 60, and in particular the angled segments 72 and 73 that meet up at transition regions 80, facilitates the indirect compression of the adjacent proximal apices that lack the coupling portions 65 and direct engagement with the retaining member 20.

An introducer, similar to that described in PCT application WO98/53761, entitled "A Prosthesis and a Method and Means of Deploying a Prosthesis," which is incorporated herein by reference in its entirety, may be used to deploy the stent-graft 59. PCT application WO98/53761 describes a deployment system for an endoluminal prosthesis whereby the prosthesis is radially compressed onto a delivery catheter and is covered by an outer sheath. To deploy the system, the operator slides or retracts the outer sheath over the delivery catheter, thereby exposing the prosthesis. The prosthesis expands outwardly upon removal of the sheath. The operator can directly manipulate the sheath and the delivery catheter, which provides the operator with a relatively high degree of control during the procedure. However, in the current embodiments, trigger wires and any of their associated sleeves would not be necessary to deploy the stent-graft 59. Rather, the cannula 50 and the retaining member 20 of the present embodiments may be incorporated as part of the deployment system with the stent-graft 59 being positioned coaxially between the cannula 50 and the outer sheath. A mechanism, such as a pin vise, may be employed to prevent inadvertent rotation of the cannula 50 prior to the intended rotation as described in the present application.

In operation, a wire guide may be advanced to the target site, and the cannula 50 may be advanced over the wire guide to position the apparatus at the desired location in proximity to the target site, with the atraumatic tip 55 reducing the likelihood of injury to bodily passageways during delivery. The outer sheath is disposed over the cannula 50 and the stent-graft 59 during insertion to the target site. Upon proper positioning at the target site using a desired imaging modality, the outer sheath is then retracted to expose at least a portion of the stent 60.

When the stent 60 is at least partially exposed, and it is desirable to deploy the proximal end 61 of the stent 60, the cannula 50 may be rotated in a clockwise direction until the longitudinal strut portions 66a-66d are aligned with the axial openings 42a-42d of the retaining member 20, i.e., in a reverse manner from which the longitudinal strut portions 66a-66d were loaded and secured to the retaining member 20. The proximal end 61 of the stent 60 then is allowed to self-expand due to the resilient nature of the struts, which will be inclined to move radially outward when no longer constrained by the outer wall portions 44. The remainder of the stent-graft 59 may be deployed by further retraction of the outer sheath or actuation of any other devices that are radially constraining the remainder of the stent-graft 59.

Advantageously, the proximal end 61 of the stent 60 is radially restrained without the use of convention trigger wires that span a full longitudinal length of the delivery system. Accordingly, the radial profile of the delivery system may be reduced without the provision of multiple trigger wires and one or more associated sleeves to house the trigger wires, thereby reducing packing density of the system. Moreover, deployment may be simplified as reduced deployment forces are expected to be needed relative to the use of conventional trigger wires.

As a further advantage, deployment of the stent 60 using the retaining member 20 may allow for more precise positioning of the stent 60. In particular, deployment using the retaining member 20 may provide a more controlled release of the associated portion of the stent 60, whereas the release of conventional trigger wires may require higher deployment forces that can cause a portion of the stent to jump longitudinally, thereby potentially deploying the stent offset from the intended target site.

As yet a further advantage, all of the coupling portions 65a-65d may be released from engagement with their respective axial openings 42a-42d at the same time, as a single rotational movement of the cannula 50 can automatically align each of the longitudinal strut portions 66a-66d with their respective axial openings 42a-42d. A simultaneous deployment of all of the coupling portions 65a-65d may promote a more accurate deployment at the target site.

As another advantage, the provision of projections 67a-67d may reduce inadvertent premature deployment of the coupling portions 65a-65d from their respective slots 40a-40d. In particular, the stent 60 may be inclined to move in a distal direction prior to deployment. However, the projections 67a-67d, which at least partially circumferentially and/or radially overlap with solid regions of the main body 30, are precluded from moving distally beyond the first end 31 of the retaining member 20 in the delivery state.

Figure 6A:
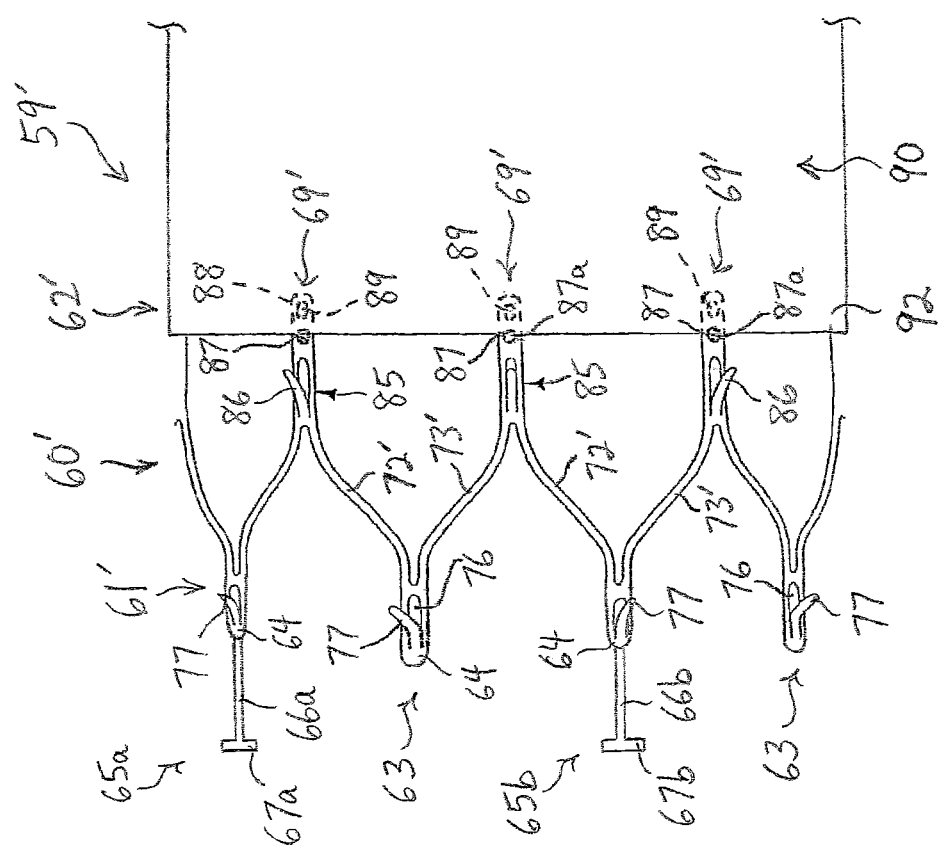
FIG. 6A depicts an alternative stent-graft having a portion that may be deployed using the retaining member of FIGS. 1-4.

Referring now to FIG. 6A, an alternative stent-graft 59' comprises an alternative stent 60' that may be used with the retaining member 20 of FIGS. 1-4. The alternative stent 60' is similar to the stent 60 above, except as generally noted below. The stent 60' has proximal and distal ends 61' and 62', a series of proximal apices 63 disposed at the proximal end of the stent 60', and a series of distal apices 69' disposed at the distal end of the stent 60'. A plurality of strut segments 72' and 73' are disposed between the series of proximal apices 63 and the series of distal apices 69', as shown in FIG. 6A. The series of proximal apices 63 are each disposed proximally beyond the proximal end 92 of the graft 90, and the series of distal apices 69' of the stent 60' are each disposed distal to the proximal end 92 of the graft 90.

The first and second angled strut segments 72' and 73' meet with one another distally to form a distal transition region 85. In the embodiment of FIG. 6A, each of the distal apices 69' comprises the end region 88 having the suture bore 89 formed therein, as in the embodiment of FIG. 5. Further, each of the distal apices 69' comprises an imaging bore 87 adapted to receive an imaging element 87a, such as a radiopaque marker. The imaging bore 87 is disposed proximal to the suture bore 89, and the imaging bore 87 is adapted to be aligned with the proximal end 92 of the graft 90, thereby allowing the imaging element 87a associated with the imaging bore 87 to significantly enhance imaging directly at the proximal end 92 of the graft 90. Further, the stent 60 may comprises at least one barb 86 that is integrally formed along the distal transition region 85 at a location proximal to the imaging bore 87, as shown in FIG. 6A.

Figure 6B:
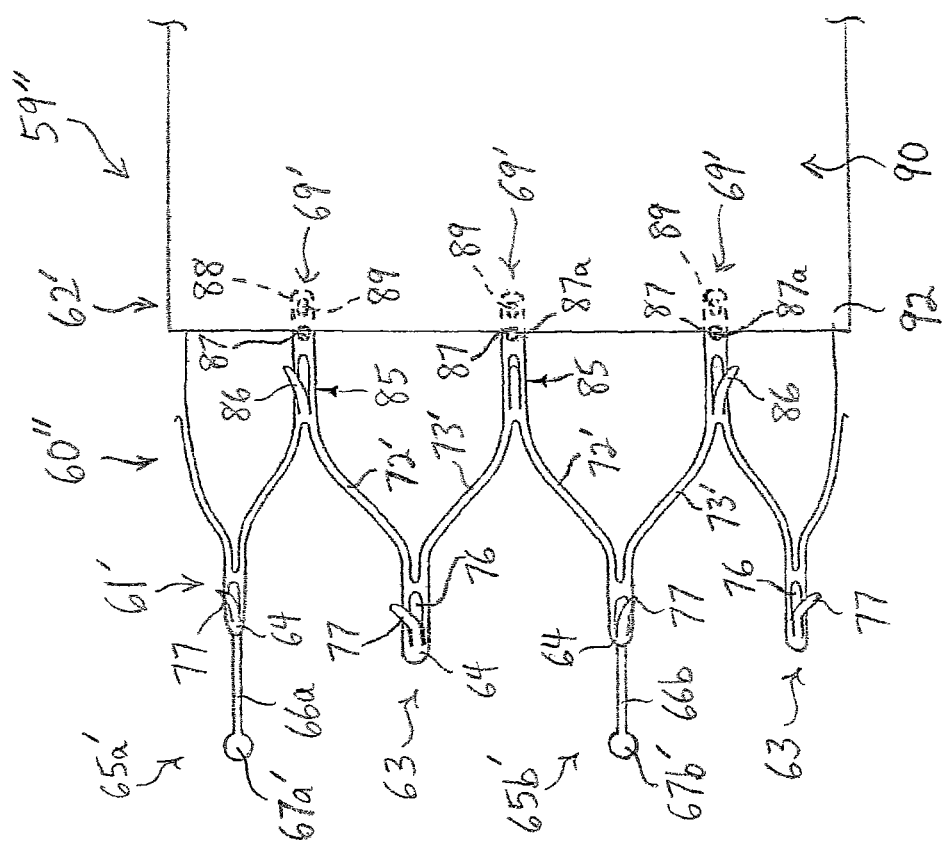
FIG. 6B depicts an alternative stent-graft having a portion that may be deployed using the retaining member of FIGS. 1-4.

Referring now to FIG. 6B, a further alternative stent-graft 59" comprises an alternative stent 60" that is similar to the stent 60' of FIG. 6A, with a main exception that alternative coupling portions are provided. In this example, exemplary coupling portions 65a' and 65b' comprise the longitudinal strut portions 66a and 66b described above, which transition into rounded projections 67a' and 67b', respectively. The function of the rounded projections 67a' and 67b' is generally the same as the projections 67a-67d described in detail above. It will be noted that while round shapes are depicted in FIG. 6B, the rounded projections 67a' and 67b' may comprise elliptical, dome, or other shapes.

Figure 8:
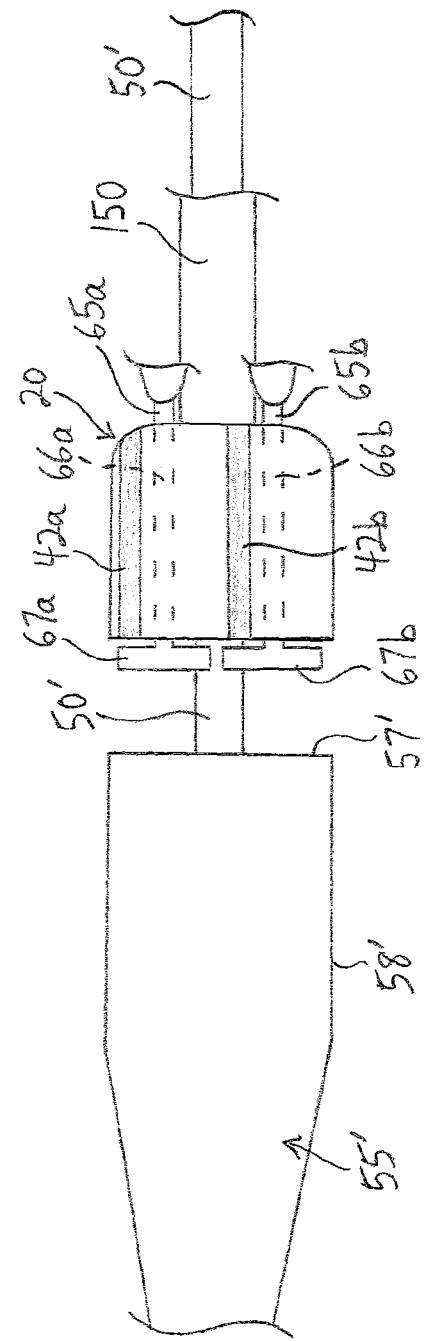

Referring now to FIGS. 7-8, in an alternative system, an inner cannula 50' and an outer cannula 150 are used in conjunction with the retaining member 20 of FIGS. 1-4. The inner cannula 50' comprises an outer diameter that is slightly less than an inner diameter of the outer cannula 150, thereby allowing relative longitudinal sliding movement between the inner cannula 50' and the outer cannula 150.

In this example, the lumen 45 of the retaining member 20 is disposed around, and secured to, an outer surface of the outer cannula 150. The inner cannula 50', after extending through the outer cannula 150, is secured to an alternative atraumatic tip 55'. The atraumatic tip 55' is similar to the atraumatic tip 55 above, except a generally flat proximal region 57' is provided adjacent to a central region 58'.

The system of FIGS. 7-8 has a first state, suitable for delivery, in which the proximal region 57' is in substantially close proximity to, or abutting, the lateral projections 67a-67d of the stent 60, as depicted in FIG. 7. In this state, the lateral projections 67a-67d are closely sandwiched between the proximal region 57' of the atraumatic tip 55' and the first end 31 of the retaining member 20. Advantageously, this closely sandwiched or abutting relationship of components may reduce the likelihood of inadvertent axial movement of the lateral projections 67a-67d, and potential inadvertent deployment of the stent 60. Moreover, in this state, the central region 58' of the atraumatic tip 55' may comprise a diameter that is substantially identical to an outer diameter of the main body 30 of the retaining member 20, and therefore the retaining member 20 is a nearly continuous extension of the shape of the atraumatic tip 55'.

When a physician is ready to deploy the stent 60, relative movement may be achieved between the inner cannula 50' and the outer cannula 150 to achieve separation between the atraumatic tip 55' and the retaining member 20. In particular, the inner cannula 50' and the atraumatic tip 55' may be advanced proximally while the outer cannula 150 and the retaining member 20 are held steady, and/or the outer cannula 150 and the retaining member 20 may be advanced distally while the inner cannula 50' and the atraumatic tip 55' are held steady, thereby achieving a state similar to the one depicted in FIG. 8. The degree of separation provided between the atraumatic tip 55' and the retaining member 20 facilitate subsequent deployment of the stent 60 from the retaining member 20. After deployment of the stent 60, the inner and outer cannulas 50' and 150 may be manipulated such that the proximal region 57' of the atraumatic tip 55' and the first end 31 of the retaining member 20 are in close proximity, or abutting one another, during removal of the system.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A method for deploying at least a portion of a stent, the method comprising:
   providing a retaining member comprising a main body having first and second ends, and at least one slot formed into the main body, the at least one slot comprising a circumferentially enclosed segment and an axial opening;
   positioning a portion of a stent within the axial opening of the retaining member, and subsequently within the circumferentially enclosed segment, thereby radially restraining the portion of the stent in a compressed state; and rotating the retaining member relative to the stent, thereby aligning the portion of the stent with the axial opening and permitting the stent to self-expand radially outward, wherein, during the step of rotating the retaining member, a wall portion of the retaining member is circumferentially rotated over the portion of the stent being restrained within the retaining member.

2. The method of claim 1 further comprising providing a cannula having an outer surface, where at least a portion of the retaining member is secured to the outer surface of the cannula.

3. The method of claim 1, where the stent comprises at least one coupling portion comprising a longitudinal strut portion having a first width that is less than a second width of the axial opening of the retaining member.

4. The method of claim 3, where the coupling portion extends proximally from a proximal apex of the stent.

5. The method of claim 3, where the coupling portion further comprises at least one of a lateral or rounded projection.

6. The method of claim 5, where a lateral projection is provided, and the longitudinal strut portion and the lateral projection of the coupling portion collectively form a "t" shape.

7. The method of claim 5 further comprising positioning the at least one of a lateral or rounded projection proximal to a proximal end of the main body of the retaining member when the stent is restrained.

8. A method for deploying at least a portion of a stent, the method comprising:
   providing a retaining member comprising a main body having first and second ends, and at least one slot formed into the main body, the at least one slot comprising a circumferentially enclosed segment and an axial opening;
   positioning a portion of a stent within the axial opening of the retaining member, and subsequently within the circumferentially enclosed segment, thereby radially restraining the portion of the stent in a compressed state; and
   rotating the retaining member relative to the stent, thereby aligning the portion of the stent with the axial opening and permitting the stent to self-expand radially outward,
   wherein rotation of the retaining member relative to the stent occurs without a corresponding circumferential twisting motion of the stent.

9. The method of claim 8 further comprising providing a cannula having an outer surface, where at least a portion of the retaining member is secured to the outer surface of the cannula.

10. The method of claim 8, where the stent comprises at least one coupling portion comprising a longitudinal strut portion having a first width that is less than a second width of the axial opening of the retaining member.

11. The method of claim 10, where the coupling portion extends proximally from a proximal apex of the stent.

12. The method of claim 10, where the coupling portion further comprises at least one of a lateral or rounded projection.

13. The method of claim 12, where a lateral projection is provided, and the longitudinal strut portion and the lateral projection of the coupling portion collectively form a "t" shape.

14. The method of claim 12 further comprising positioning the at least one of a lateral or rounded projection proximal to a proximal end of the main body of the retaining member when the stent is restrained.

15. A method for deploying at least a portion of a stent, the method comprising:
   providing a retaining member comprising a main body having first and second ends, and at least one slot formed into the main body, the at least one slot comprising a circumferentially enclosed segment and an axial opening;
   positioning a portion of a stent within the axial opening of the retaining member, and subsequently within the circumferentially enclosed segment, thereby radially restraining the portion of the stent in a compressed state; and
   rotating the retaining member relative to the stent, thereby aligning the portion of the stent with the axial opening and permitting the stent to self-expand radially outward,
   wherein the stent extends axially beyond the first and second ends of the retaining member in the compressed state.

16. The method of claim 15 further comprising providing a cannula having an outer surface, where at least a portion of the retaining member is secured to the outer surface of the cannula.

17. The method of claim 15, where the stent comprises at least one coupling portion comprising a longitudinal strut portion having a first width that is less than a second width of the axial opening of the retaining member.

18. The method of claim 17, where the coupling portion extends proximally from a proximal apex of the stent.

19. The method of claim 17, where the coupling portion further comprises at least one of a lateral or rounded projection.

20. The method of claim 19, where a lateral projection is provided, and the longitudinal strut portion and the lateral projection of the coupling portion collectively form a "t" shape.

* * * * *